United States Patent [19]

Ritter et al.

[11] 4,400,380

[45] Aug. 23, 1983

[54] ANTIVIRAL 1-ARYL-5-AMINO-1-PENTEN-3-ONES

[75] Inventors: Harry W. Ritter, Loveland; Michael L. Edwards, Cincinnati, both of Ohio

[73] Assignee: Merrell Dow Pharmaceuticals Inc., Cincinnati, Ohio

[21] Appl. No.: 276,139

[22] Filed: Jun. 22, 1981

Related U.S. Application Data

[63] Continuation-in-part of Ser. No. 165,430, Jul. 2, 1980, abandoned.

[51] Int. Cl.³ .............. A61K 31/445; A61K 31/40
[52] U.S. Cl. .............. 424/248.5; 260/465 E; 424/248.52; 424/248.57; 424/250; 424/274; 424/285; 424/304; 424/329; 424/330; 424/267; 542/438; 542/439; 542/440; 564/284; 564/287; 564/288; 564/342; 564/344; 564/345; 549/444
[58] Field of Search ........... 424/248.57, 248.5, 248.52, 424/304, 330, 329, 367, 250, 274, 285; 564/342, 344, 345, 284, 287, 288; 542/438, 439, 440; 260/340.5, 465 E

[56] References Cited

U.S. PATENT DOCUMENTS 2,993,890 7/1961 Shapiro et al. .............. 542/439
4,209,517 6/1980 Riveron .............. 424/248.57

OTHER PUBLICATIONS

Gvozdjakova et al., Chem. Abst. 76 (1972), #99583.

Primary Examiner—Arthur P. Demers
Attorney, Agent, or Firm—Raymond A. McDonald; Gary D. Street; William J. Stein

[57] ABSTRACT

Compounds of the formula

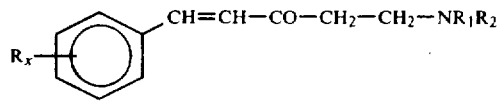

wherein
R is H, halo, $C_{1-4}$ alkyl, $C_{1-4}$ alkoxy, 3,4-methylenedioxy, $CF_3$, $NO_2$, $NH_2$, $N(C_{1-4}$ alkyl$)_2$, CN, OH, —S($C_{1-4}$ alkyl) or —SO$_2$($C_{1-4}$ alkyl); $R_1$ and $R_2$ are independently each H or $C_{1-4}$ alkyl or taken together with the attached N atom are morpholino, piperidino, pyrrolidino, piperazino, or N— $C_{1-4}$-alkyl piperazino; and, when R is halo, $C_{1-4}$ alkyl or $C_{1-4}$ alkoxy, x is 0-3 and, otherwise, is 0 or 1;
or a pharmaceutically acceptable salt thereof with an acid or for the compounds wherein $R_1$ and $R_2$ are both not H, a quaternary ammonium salt thereof with a $C_{1-4}$ alkyl halide
have valuable antiviral activity, e.g., for treatment of infections caused by a herpes virus.

8 Claims, No Drawings

ANTIVIRAL 1-ARYL-5-AMINO-1-PENTEN-3-ONES

This application is a continuation-in-part application of our co-pending application Ser. No. 165,430, filed July 2, 1980 (not abandoned).

BACKGROUND OF THE INVENTION

This invention relates to 1-aryl-5-amino-1penten-3-ones having antiviral activity.

Many 1-aryl-5-amino-1-penten-3-ones are known. Several pharmacological activities are reported for such compounds. However, there has been no suggestion that such compounds, either known or heretofore unknown, might possess antiviral activity.

SUMMARY OF THE INVENTION

Accordingly, it is an object of this invention to provide a new method of using 1-aryl-5-amino-1-penten-3-ones as well as new classes of such compounds and of pharmaceutical compositions containing them.

Upon further study of the specification and appended claims, further objects and advantages of this invention will become apparent to those skilled in the art.

These objects, in one aspect of this invention, have been attained by providing a method of treating a viral infection which is amenable to topical treatment comprising topically treating a patient suffering from such a viral infection with an antivirally effective amount of a compound of Formula I

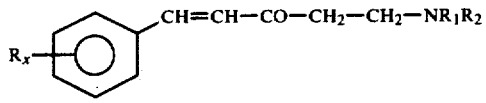

wherein
R is H, halogen (F, Cl, Br, I), $C_{1-4}$ alkyl, $C_{1-4}$ alkoxy, 3,4-methylenedioxy, $CF_3$, $NO_2$, $NH_2$, $N(C_{1-4}$ alkyl$)_2$, CN, OH, —S($C_{1-4}$ alkyl) or —$SO_2$($C_{1-4}$ alkyl); $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; and, when R is halo, $C_{1-4}$ alkyl or $C_{1-4}$ alkoxy, x is 0–3 and, otherwise, is 0 or 1;
or a pharmaceutically acceptable salt thereof with an acid or, for the compounds wherein $R_1$ and $R_2$ are not H, the quaternary ammonium salts thereof In another aspect, these objects have been achieved by providing pharmaceutical compositions comprising a pharmaceutically acceptable adjuvant and an antivirally effective amount e.g., an amount effective for treating herpesvirus topically, of a compound of Formula I above wherein when R is H, $R_1$ and $R_2$ are both H or together with the attached N atom are piperazino or N-$C_{1-4}$-alkyl piperazino; when R is chloro, $R_1$ and $R_2$ are both H or together with the N atom to which they are attached are morpholino, pyrrolidino, piperidino, piperazino or N-$C_{1-4}$-alkyl piperazino; when R is bromo $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is fluoro, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is iodo, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is $C_{1-4}$ alkyl, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is $C_{1-4}$ alkoxy, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is 3,4-methylenedioxy, $R_1$ and $R_2$ independently are H or $C_{1-4}$ alkyl or together with the N atom to which they are attached are pyrrolidino, piperidino, piperazino or N-$C_{1-4}$-alkyl piperazino; when R is $CF_3$, $R_1$ and $R_2$ are independently each H or $C_{1-4}$ alkyl or taken together with the attached N atom are morpholino, piperidino, pyrrolidino, piperazino, or N-$C_{1-4}$alkyl piperazino; when R is $NO_2$, $R_1$ and $R_2$ are independently each H or $C_{1-4}$alkyl or taken together with the attached N atom are morpholino, piperidino, pyrrolidino, piperazino, or N-$C_{1-4}$-alkyl piperazino; when R is $OH_2$, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is N($C_{1-4}$ alkyl$)_2$, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is CN, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is OH, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is —S-$C_{1-4}$-alkyl, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is $SO_2$-$C_{1-4}$-alkyl, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino. As above, when R is halo, $C_{1-4}$ alkyl or $C_{1-4}$ alkoxy, x is 0–3 and, otherwise, is 0 or 1. Also included within the scope of these pharmaceutical compositions, are the pharmaceutically acceptable salts of the compounds described above with an acid or, for the compounds wherein $R_1$ and $R_2$ are not H, the quaternary ammonium salts thereof.

In yet another aspect of this invention, these objects have been attained by providing novel quaternary ammonium salts of the bases of the aryl amino pentenones of Formula I above when $R_1$ and $R_2$ are both other than H, and the bases and pharmaceutically acceptable salts thereof wherein when R is H, $R_1$ and $R_2$ are both H or together with the N atom to which they are attached are piperazino and $C_{1-4}$-alkyl piperazino; when R is chloro, both $R_1$ and $R_2$ are H or together with the N atom to which they are attached are pyrrolidino, piperazino or N-$C_{1-4}$-alkyl piperazino; when R is bromo, $R_1$ and $R_2$ are independently each H or C alkyl or taken together with the attached N atom are morpholino, piperidino, pyrrolidino, piperazino, or N-$C_{1-4}$-alkyl piperazino; when R is F, $R_1$ and $R_2$ are independently each H or $C_{1-4}$alkyl or taken together with the attached N atom are morpholino, piperidino, pyrrolidino, piperazino, or N-$C_{1-4}$-alkyl piperazino; when R is I, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is $C_{1-4}$ alkyl, $R_1$ and $R_2$ are both H or together with the N atom to which they are attached are morpholino, piperidino, piperazino, or N-$C_{1-4}$-alkyl piperazino; when R is $C_{1-4}$ alkoxy, $R_1$ and $R_2$ are both H or together with the N atom to which they are attached are piperazino or N-$C_{1-4}$-alkyl piperazino; when R is 3,4-methylenedioxy, $R_1$ and $R_2$ are both H or together with the N atom to which they are attached are pyrrolidino, piperazino or N-$C_{1-4}$-alkyl piperazino; when R is $CF_3$, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is $NO_2$, $R_1$ and $R_2$ are both H or together with the N atom to which they are attached are piperazino or N-$C_{1-4}$-alkyl piperazino; when R is $NH_2$, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is N($C_{1-4}$-alkyl)$_2$, $R_1$ and $R_2$ independently are each H or $C_{1-4}$ alkyl or together with the N atom to which they are attached are pyrrolidino, piperazino or N-$C_{1-4}$-alkyl piperazino; when R is CN, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino; when R is OH, $R_1$ and $R_2$ are both H or together with the N atom to which they are attached are piperazino or N-$C_{1-4}$-alkyl piperazino; when R is -S-$C_{1-4}$ alkyl, $R_1$ or $R_2$ are independently each H or $C_{1-4}$ alkyl or taken together with the attached N atom are morpholino, piperazino, pyrrolidino, piperazino, or N-$C_{1-4}$-alkyl piperazino, and when R is -$SO_2$-$C_{1-4}$ alkyl, $R_1$ and $R_2$ are independently each H or $C_{1-4}$ alkyl or taken together with the attached N atom are morpholino, piperidino, pyrrolidino, piperazino, or N-$C_{1-4}$-alkyl piperazino. As above, when R is halo, $C_{1-4}$ alkyl or $C_{1-4}$ alkoxy, x is 0-3 and, otherwise, is 0 or 1. Also included are the pharmaceutically acceptable salts of these compounds with an acid.

DETAILED DISCUSSION

In all of the compounds per se of this invention as well as those in the compositions and methods of use of this invention, suitable alkyl moieties in the R, $R_1$ and $R_2$ groups (i.e., the $C_{1-4}$ alkyl groups per se as well as those which form a part of the $C_{1-4}$ alkoxy, N($C_{1-4}$-alkyl)$_2$, S($C_{1-4}$alkyl), $SO_2$($C_{1-4}$alkyl) and N-$C_{1-4}$-alkyl piperazino groups), include methyl, ethyl, propyl, isopropyl, n-butyl, isobutyl, sec-butyl and tert-butyl. When R is N($C_{1-4}$alkyl)$_2$, the two alkyl groups may be the same or different, any combination of two of the mentioned alkyl groups being suitable. Similarly, $R_1$ and $R_2$ may be the same or different, any combination of the mentioned alkyl groups with each other or hydrogen being suitable.

Accordingly, suitable alkoxy groups as R include methoxy, ethoxy, propoxy, isopropoxy, n-butoxy, isobutoxy, sec-butoxy and tert-butoxy. Suitable dialkyl amino groups include dimethylamino, diethylamino, dipropylamino, dibutylamino, etc., N-methyl-N-ethylamino, N-methyl-N-propylamino, etc. Suitable mercapto groups include methylthio, propylthio, etc., and suitable sulfonyl groups include methylsulfonyl, ethylsulfonyl, isopropylsulfonyl, etc.

Suitable halo atoms as R include F, Cl, Br and I.

In general, on the phenyl ring to which R is attached, no substitution (R=H) or monosubstitution (x=1) in the 3- or 4-position is preferred. For R is halo, $C_{1-4}$ alkyl or $C_{1-4}$ alkoxy, disubstitution is also preferred, e.g., in the 3,4-positions. Combinations of two or more identical substituents are also possible.

As R, preferred are H and halo (especially Cl).

The quaternary ammonium salts of the compounds of Formula I wherein both $R_1$ and $R_2$ are not H include those which are formed with, e.g., alkyl halides such as alkyl iodides, alkyl chlorides or alkyl bromides. Suitable alkyl moieties include those mentioned above in conjunction with the R, $R_1$ and $R_2$ moieties. Also included are those quaternaries prepared from the sulfonic acids such as methyl sulfonic acid, toluenesulfonic acid and the like, as well as any of the normal prior art quaternary salts generally utilized for pharmaceutical formulation benefits. The preferred quaternaries are those formed with lower alkyl halides.

$NR_1R_2$ is preferably dialkylamino, e.g., dimethylamino, or morpholino. Preferred compounds are those wherein combinations of the preferred embodiments of $NR_1R_2$ and $R_x$ are contained, e.g., $NR_1R_2$ is morpholino and $R_x$ is H, $NR_1R_2$ is morpholino and $R_x$ is 3,4-dichloro, etc.

The hydrochloride salts, in general, are the preferred salts as well as the preferred forms of the compounds of this invention.

Illustrative examples of the compounds of this invention include the following:

5-(4-morpholinyl)-1-phenyl-1-penten-3-one;
5-(4-morpholinyl)-1-(3,4-dichlorophenyl)-1-penten-3-one;
5-(4-morpholinyl)-1-(3-trifluoromethylphenyl)-1-penten-3-one;
5-(4-morpholinyl)-1-(2,6-dichlorophenyl)-1-penten-3-one;
5-(4-morpholinyl)-1-(1,3-benzodioxyl-5-yl)-1-penten-3-one;
5-(4-morpholinyl)-1-(4-(methylthio)phenyl)-1-penten-3-one;
5-(4-morpholinyl)-1-(4-(methylsulfonyl)phenyl)-1-penten-3-one;
5-(4-morpholinyl)-1-(4-chlorophenyl)-1-penten-3-one;
5-(4-morpholinyl)-1-(4-cyanophenyl)-1-penten-3-one;
E-N,N,N-trimethyl-3-oxo-5-phenyl-4-penten-1-aminium iodide;
5-methylamino-1-phenyl-1-penten-3-one;
5-dimethylamino-1-(2-ethylphenyl)-1-penten-3-one;
5-(1-piperidino)-1-(2,4-dipropylphenyl)-1-penten-3-one;
5-(1-piperidino)-1-(2,4,6-trimethylphenyl)-1-penten-3-one;
5-(1-pyrrolidino)-1-(4-n-butoxyphenyl)-1-penten-3-one;
5-(1-piperazino)-1-(4-aminophenyl)-1-penten-3-one;
5-(4-ethylpiperazino-1-yl)-1-(4-nitrophenyl)-1-penten-3-one;
5-amino-1-(3-dimethylaminophenyl)-1-penten-3-one;
5-(4-morpholinyl)-1-(4-hydroxyphenyl)-1-penten-3-one; and
5-(4-morpholinyl)-1-(2-methyl-4-chlorophenyl)-1-penten-3-one.

Illustrative examples of the compounds of this invention also include the hydrochloride salts of each of the foregoing compounds, e.g., 5-(4-morpholinyl)-1-phenyl-1-penten-3-one hydrochloride and the compounds prepared in the examples.

The compounds of this invention are useful as topical antiviral agents. For example, they may be used in the topical treatment of *Herpesvirus hominis*, a DNA virus, which causes disease for which, at the present time, there is no completely adequate treatment; Vaccinia, Cytomegalovirus; and other DNA viruses which are amenable to topical treatment.

The compounds of this invention may be used in the control of all manifestations of *Herpesvirus hominis* which are amenable to topically administered agents, which excludes, e.g., herpes encephalitis and generalized infections. Herpesvirus-induced indications which may be treated using the compounds of this invention include acute gingivostomatitis, *Herpes labialis*, outer eye infections, such as keratoconjunctivitis, *Herpes genitalia*, neonatal herpes, etc. Both *Herpesvirus hominis*, type 1 and *Herpevirus hominis*, type 2 are amenable to topical control using the compounds of this invention. Both types are capable of infecting either the upper sites of the body or the genitalia. Additionally, chicken pox, a primary infection caused by a herpes virus (Varicella-Zoster) and its secondary manifestation, shingles (*Herpes-Zoster*) can also be topically treated with the compounds of this invention.

The compounds of this invention may be applied in various topical formulations to the infected site in the host suffering, e.g., from the effects of *Herpesvirus hominis*, e.g., a mammal or other animal, including humans and rats, cats, dogs, pigs, cattle, horses, rabbits, fowl, etc. As used herein, the term "patient" is intended to mean the animal or mammal being treated.

The active compounds of this invention are generally included in topical formulations in a concentration of 1-10% based upon the total weight of the formulation, generally 1-6% and, usually, optimally of about 2-4% on the same basis, especially for treatment of the epidermis. For treatment of occular manifestations of the herpes or other virus being treated, concentrations of usually 0.1-1%, preferably 0.2-0.5%, are employed. However, in all applications, greater or lesser concentrations may be employed where suitable, e.g., higher concentrations may be employed in the mentioned occular formulations where irritation of the eye does not ensue. The compounds of this invention are topically administered at these concentrations generally 2-8 times per day, preferably 3-4 times per day, as needed. Details of the administration are analogous, in general, to that of such conventional antiviral agents as Vira-A ® (adenosine arabinoside; Ara A Park-Davis).

The compounds of this invention may be employed in human and veterinary medicine for the indications mentioned above in any of the conventional forms for topical application, such as solutions, suspension, lotions, emulsions, creams, ointments, plasters, powders, linaments, salves, aerosols, gels, etc., such that an antivirally effective amount of the compound of this invention is applied. The amount of topical formulation which is administered will depend upon the activity of the particular compound employed and on the severity of the infection and the other fully conventional factors. The amount of active ingredient will be as described above and the amount of topical formulation, e.g., will generally be sufficient to coat the area to be treated.

In general, these topical formulations are non-sprayable, viscous to semi-solid or solid forms comprising a carrier indigenous to topical application and having a dynamic viscosity, preferably greater than that of water. In solid dosage forms, it is often desirable to micronize the compound of this invention to be combined with the various conventional carriers, for example, binders, such as acacia, corn starch or gelatin, disintegrating agents, such as corn starch, guar gum, potato starch or algenic acid, lubricants, such as stearic acid or magnesium stearate, and inert fillers, such as lactose, sucrose or corn starch. Suitable carriers for liquid formulations such as suspensions or solutions, which can optionally be sterile, include oil, water, an alcohol or mixtures thereof, with or without the addition of a pharmaceutically suitable surfactant, suspending agent, or emulsifying agent. These can be used for spreading on the skin or administration to the eye, e.g., as an eye drop. Where suitable, they may contain emolients, perfumes, or moisturizing pigments, etc. to form cosmetically desirable preparations. Such liquid preparations can be formulated suitably with oils, such as fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides; with alcohols such as ethanol, isopropanol, hexadecyl alcohol, glycerol and propylene glycol; with glycerol ketals, such as 2,2-dimethyl-1,3-dioxolane-4-methanol; with ethers, such as polyethylene glycol 400; with petroleum hydrocarbons, such as mineral oil and petrolatum; with water; or with mixtures thereof; with or without the addition of a pharmaceutically suitable surfactant, suspending agent or emulsifying agent.

Where appropriate, the topical preparations can also be formulated in the form of soaps and synthetic detergents using conventional carriers for the same. Suitable such soaps include fatty acid alkali metal, ammonium and triethanol amine salts. Suitable detergents include cationic detergents, for example, dimethyl dialkyl ammonium halides, alkyl pyridinium halides, and alkyl amine acetates; anionic detergents, for example, alkyl, aryl and olefin sulfonates, alkyl, olefin, ether and monoglyceride sulfates, and sulfur succinates; non-ionic detergents, for example, fatty amine oxides, fatty acid alkanol amides, and polyoxyethylene polyoxypropylene copolymers; and amphoteric detergents, for example, alkyl betaminopropionates and 2-alkyl imidazoline quaternary ammonium salts; and mixtures thereof. Detergent compositions may be in bar, powder or liquid form and may incorporate foam builders, viscosity control agents, preservatives, emolients, coloring agents, perfumes and solvents.

Aerosol or spray topical preparations may contain a micronized solid or a solution of a compound of this invention and may also contain solvents, buffers, surfactants, perfumes antioxidants and propellants. They may be applied by means of a propellant under pressure or by means of a compressable plastic spray bottle, a nebulizer or an atomizer without the use of a gaseous propellant.

The topical compositions of this invention may also be formulated with other active ingredients such as local anesthetics, such as benzocaine, benzyl alcohol and phenol and their pharmaceutically acceptable salts, as well as antibacterials.

The active compounds of this invention may also be administered by means of a sustained release system whereby they are gradually released at a controlled, uniform rate from an inert or bioerodable carrier by means of diffusion, osmosis, or disintegration of the carrier during the treatment. Such controlled release drug delivery systems may be in the form of patches or bandages applied to the skin or occular inserts placed in the cul de sac of the eye. Such systems permit the treated area to be exposed constantly for prolonged time to a therapeutically effective dosage of a compound of this invention. The unit dosage of the compound administered by means of a sustained release system will approximate the amount of an effective daily dosage multiplied by the maximum number of days during which the carrier is to remain on the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polysiloxanes, and polyimides in mixtures, laminae and copolymers thereof. The compounds of this invention may be incorporated in the sustained release carrier in a pure form or may be dissolved in any suitable liquid or solid vehicle, including the polymer of which the sustained release carrier is formed.

The antiviral activity of the compounds of this invention can be demonstrated in any of several known test systems. For example, in vivo antiviral activity may be demonstrated in the nonfatal Herpesvirus paralysis mouse model. The skin at the base of the tail of the mouse (CD-1 strain; males; 18–20 g) is scratched and the scarified site is infected with *Herpesvirus homonis*, type 1 by application with a sterile cotton swab that has been dipped into an innoculum preparation of the same. Ten mice per group are included. A severe hind limb paralysis occurs in untreated mice, usually, at six to eight days after application, day one being considered the day of infection. The mice are treated with the test compound 2, 4 and 6 hours after challenge by topical application with a sterile cotton swab that has been dipped into the test compound preparation. Twenty mice are included in the infected vehicle-treated control group. The animals are observed for 11 days or until paralysis, the end point, is noted. The vehicle is 1.4% polyvinyl alcohol in sterile distilled water. For example, under these test conditions, when applfied in topical doses of 3%, 5-(4-morpholinyl)-1-phenyl-1-penten-3-one hydrochloride, 1-(3,4-dichlorophenyl)-5-morpholen-4-yl-1-penten-3-one hydrochloride, 5-(4-morpholinyl)-1-(3-(trifluoromethyl)phenyl)-1-penten-3-one hydrochloride, 1-(2,6-dichlorophenyl)-5-(4-morpholinyl-1-penten-3-one hydrochloride, 1-(1,3-benzodioxyl-5-yl)-5-(4-morpholinyl)-1-penten-3-one hydro E-N,N,N-trimethyl-3-oxo-5-phenyl-4-penten-1-aminium iodide and 1-phenyl-5-(dimethylamino)-1-penten-3-one hydrochloride gave the following percentages of mice paralyzed, respectively: 0%, 0%, 40%, 10%, 10%, 10% and 10%. Significant antiviral activity was also established in this test for, e.g., the first two mentioned compounds at lower dosages such as 0.25% and above. (In all cases, phosphonoacetate was used as the standard test compound whose activity was also demonstrated in accordance with the regimen.)

The antiviral activity of the compounds of this invention has also been established in the non-fatal hairless mouse lesion test. Hairless mice are innoculated with *Herpesvirus hominis*, type 1 by application via sterile swabs as described above to the lumbar region of the back of the mice, scarified by scratching. The test compounds are applied in optimal doses in a 1.4% solution of polyvinyl alcohol. The mice (male or female) are of the HRS/J strain (18–20 g). During the experiment, they are housed six per cage with food and water ad libitum. In untreated animals, severe ulcerated dermal lesions that follow the nerve pathway to the hind legs will develop by the eighth day after infection. These lesions are scored subjectively as to their degree of severity, i.e., 0 indicating no lesion, to a maximal lesion having a score of 3 (e.g., severe infection, lesions covering one-half or more of the lumbar region). The percent control of lesions is given as 100x the average lesion score for the test group divided by the average lesion score for the control group to which there is administered only the carrier.

Using this procedure, the antiviral activity of 1-(3,4-dichlorophenyl)-5-morpholin-4-yl-1-penten-3-one hydrochloride was demonstrated: at doses of 6% and 3%, 87% inhibition of lesions was detected; and at doses of 1.5% and 0.75%, 81% inhibition of lesions was detected. The results for 5-(4-morpholinyl)-1-phenyl-1-penten-one hydrochloride were (dose (%)/% inhibition of lesions): 3/94; 1.5/88; 0.75/76; and 0.37/70. Disodiumphosphonoacetate was again used as the standard test compound whose activity was also demonstrated using this regimen (5% in 1.4% polyvinyl alcohol).

The compounds of this invention may be prepared by subjecting the corresponding compound of Formula II to the well-known Mannich reaction as follows:

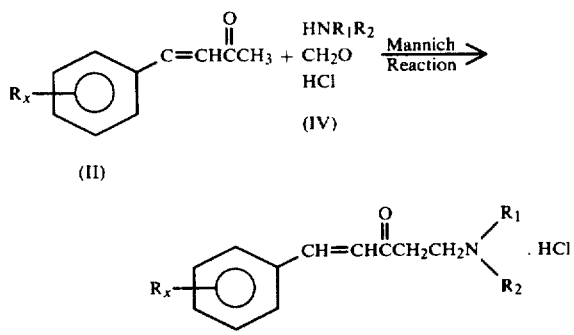

Conditions suitable for conduction of these Mannich reactions are fully conventional, e.g., see Mannich et al, Arch. Pharm., 265 684 (1928).

The Mannich reaction is generally conducted using one equivalent of each of the compounds of Formulae II and IV, along with 1–2 equivalents of formaldehyde.

The reaction is usually run in a solvent such as ethanol, acetic acid, 2-propanol or n-propanol, preferably ethanol. In a typical run, a mixture of HCl in ethanol (in a weight ratio of generally around 1:5) is first prepared and the amine and formaldehyde are added to it. The reaction mixture is refluxed (generally 70°–80° C.) for a time of up to 18 hours, typically 16–18 hours. Thereafter, the mixture is cooled and diluted with, e.g., ether or acetone, preferably acetone (about 4–5 volumes based upon the reaction volume). In general, the hydrochloride salt of the compound of Formula I precipitates. The free base can be liberated from the hydrochloride salt by conventional treatment with a strong base, e.g., NaOH. After dilution with water, the compound of Formula I can be extracted with a solvent such as chloroform, ether, ethylacetate, etc. The obtained compound may then be worked-up using conventional methods, such as those described in the examples.

Alternatively, the Mannich reaction may be carried out in acetic acid by adding the compound of Formula II to formaldehyde and the acid addition salt of the compound of Formula II and HCl, which is the preferred mode for compounds such as dimethylamine which is a gas.

The Mannich reaction is generally applicable to the production of all the compound of Formula I except for these wherein R is $NH_2$. The corresponding $NH_2$ compound is prepared, e.g., as discussed below from the corresponding $NO_2$ compound by suitable reduction thereof.

The intermediate amines of Formula IV are all known compounds, as are many of the ketones of Formula II. The latter can all be prepared using fully conventional processes such as reaction of methyl lithium with the corresponding compound of Formula III as follows:

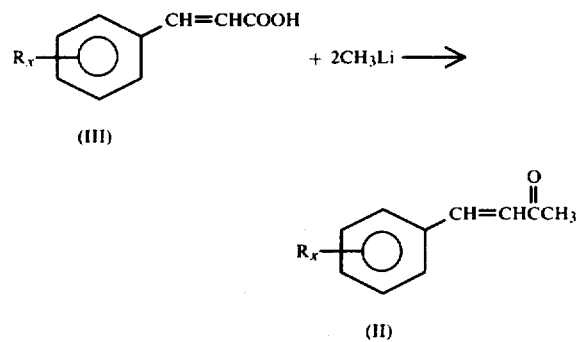

or by reacting acetone with an aldehyde of Formula V in a conventional aldol condensation using a typical catalyst such as sodium hydroxide, in accordance with the following reaction

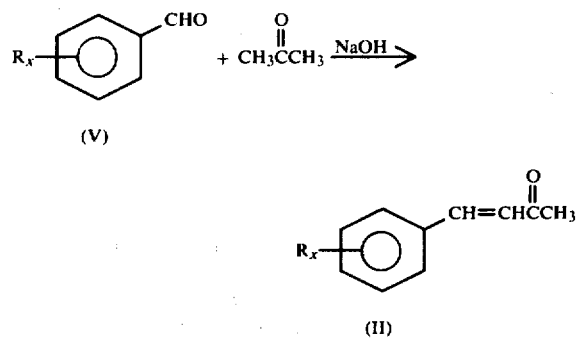

The former reaction is carried out using two equivalents of methyl lithium for each equivalent of acid of Formula III, one equivalent being required to form the lithium salt and the other to form the product ketone. The reaction is typically carried out in the presence of a solvent such as an ether, i.e., dimethoxyethane, diethylether, dioxane, etc. For each specific case, the reaction is started out in an ice bath in order to determine whether or not the reaction proceeds at such a low temperature. The reaction mixture is then gently warmed in order to accelerate the reaction. In general, suitable temperatures are 0°-40° C., up to the boiling point of the solvent. The reactions are usually conducted at room temperature by adding methyl lithium (e.g., in a commercial 1.8 M concentration in ether) dropwise to a solution of the compound of Formula III in the solvent. Reaction times are generally 2-4 hours. After completion, the reaction medium is poured into 1-2 volumes of a saturated solution of ammonium acetate in order to neutralize the lithium. Two layers are obtained, the product being in the ether layer. After extraction with an aqueous base such as sodium bicarbonate in order to remove the unreacted compound of Formula III, the ether layer is dried over magnesium sulfate and the ether is evaporated. The product of Formula II is then recrystallized or distilled depending on whether the product is a solid or liquid. This reaction is applicable to preparation of most of the intermediates of Formula II except those wherein R is a reactive group, e.g., OH, $NH_2$, CN and alkylsulfonyl. However, for example, the alkyl sulfonyl-containing compound of Formula I may be obtained by oxidizing the corresponding R-S-substituted compound of Formulae II or I, e.g., with two equivalents of metachloroperbenzoic acid at a temperature of 10°-60° C. for 2-20 hours. The amino-substituted compounds, for example, may be formed by first preparing the corresponding $NO_2$-containing compound and conventionally reducing the corresponding compound of Formula II or I using, e.g., Fe and HCl in alcohol/water.

The aldol condensation is carried out under conventional conditions whose details are readily determinable by conventional considerations and/or routine experimentation. The concentration of catalytic base appropriate in a given case will depend upon the nature of the R-group. For example, when R is methylenedioxy, a small amount of base (e.g., about 0.3 mole per mole of aldehyde) in a large volume of water (e.g., about 300 ml per 0.1 mole of aldehyde), is employed; when R is OH, a stronger base is used, e.g., about 50% NaOH. In general, from ½ to 1 volume of a solution of about 50% NaOH is employed per 3 volumes of acetone. In carrying out the reaction, typically, the aldehyde of Formula V, dissolved in from 4-8 volumes of acetone (generally 0.1-0.01 equivalents of aldehyde per eqivalent of acetone are employed), is added to the aldol condensation catalyst. A two-phase mixture is obtained. The reaction is run with agitation at a temperature generally below 40° C., preferably 0°-40° C., and most preferably 20°-30° C., for a time of up to 18 hours in general, usually at least 2-3 hours and preferably 12-16 hours. The product is usually a solid which crystallizes out and is subsequently recrystallized. If not, the reaction medium can be extracted with an organic solvent such as chloroform, diethyl ether, ethyl acetate, methylene chloride, an aromatic hydrocarbon such as benzene, trichlorobenzene, etc. If the product is a liquid, it is vacuum-distilled.

Some of the intermediates of Formula II are commercially available, e.g., that wherein R is H. The staring materials of Formulae III and V are all conventional compounds and are either commercially available or conventionally preparable by fully conventional procedures such as these disclosed in R. T. Morrison and K. N. Boyd, *Organic Chemistry*, Allyn and Bacon, Boston, Mass. (1976), whose disclosure is incorporated by reference herein.

The acid addition salts of the compounds of Formula I can be prepared in fully conventional fashion by treating a compound of Formula i with an acid which yields a pharmaceutically acceptable salt. For example, 1-10 equivalents of acid per equivalent of compound of Formula I can be added to the latter at a temperature of −5–80° C., typically room temperature, and the reaction conducted for 0.1–5 hours. The reaction is usually conducted in a solvent such as ethylalcohol, water, ether, etc. Suitable acid addition salts include those derived from the following acids: any suitable inorganic or organic acid, e.g., suitable inorganic acids include, for example, hydrochloric, hydrobromic, sulfuric or phosphoric acid, etc.; suitable organic acids include, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cynnamic, salicylic and 2-phenoxybenzoic, or sulfonic acids such as, for example, methanesulfonic, 2-hydroxyethane sulfonic acid, etc.

The quaternary ammonium salts may be prepared by reacting a compound of Formula I with an alkyl halide at a temperature of 20°–40° C. for about 72 hours in a solvent such as ether, ethyl alcohol, methyl alcohol, methyl ethyl ketone, etc. For the heterocyclic $NR_1R_2$ groups, e.g., morpholino, the reaction should be run neat at 20°–70° C. for 12–72 hours. Other quaternary salts are prepared by standard techniques well known in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

A. 5-(4-Morpholinyl)-1-phenyl-1-penten-3-one hydrochloride: A mixture of commercially available (Aldrich) 4-phenyl-3-buten-2-one (7.3 g, 0.05 mole), paraformaldehyde (2.3 g), morpholine (4.4 g, 0.05 mole) and concentrated HCl (5 ml) in ethanol (25 ml) is heated at reflux temperature for 4 hours. The reaction mixture is cooled to room temperature, diluted with acetone to 1 liter and the acetone dilution maintained at 0° C. overnight (about 16 hours). The resultant precipitate of 5-(4-morpholinyl)-1-phenyl-1-penten-3-one hydrochloride is collected by filtration and recrystallized from a minimum quantity of ethanol; m.p. 158°–159° C.

B. The foregoing procedure is repeated except that an equivalent amount of each of diethylamine and N-methylpiperazine is substituted for the morpholines used therein to yield, as respective products, 5-diethylamino-1-phenyl-1-penten-3-one hydrochloride and 5-(N-methylpiperazinyl)-1-phenyl-1-penten-3-one hydrochloride.

EXAMPLE 2

Each of the three hydrochloride salts obtained in Example 1 is neutralized with an equivalent amount of 10% aqueous sodium hydroxide and extracted with diethyl ether. The ether extract is then dried and concentrated to afford the corresponding free base, respectively. Subsequent treatment with an appropriate acid in the standard manner affords the respective Formula I acid addition salts indicated below.

$$Ph-CH=CH-\overset{\overset{O}{\|}}{C}-CH_2CH_2-NR_1R_2 \cdot salt$$

| Compound | $NR_1R_2$ | Salt |
|---|---|---|
| a. | morpholino (N/O ring) | hydrobromide |
| b. | $N(Et)_2$ | oxalate |
| c. | morpholino (N/O ring) | acetate |
| d. | N-methylpiperazino (N N—Me ring) | fumarate |
| e. | $N(Et)_2$ | nitrate |
| f. | N-methylpiperazino (N N—Me ring) | succinate |

EXAMPLE 3

A. 4-(3,4-Dichlorophenyl)-3-buten-2-one: 10 Grams of 3,4-dichlorobenzaldehyde is added to a mixture of 1 N sodium hydroxide (120 ml) and acetone (90 ml). The mixture is stirred at room temperature for 3 hours, then diluted with water (90 ml) and extracted with chloroform (2×100 ml). The combined chloroform extracts are evaporated to a gummy residue which is then distilled and the b.p. 100°/0.1 mm fraction collected, which fraction solidifies on standing to yield 4-(3,4-dichlorophenyl)-3-buten-2-one; m.p. 53°–55° C.

B. 1-(3,4-Dichlorophenyl)-5-morpholin-4-yl-1-penten-3-one hydrochloride: To 25.1 g of 4-(3,4-dichlorophenyl)-3-butene-2-one dissolved in 125 ml of ethanol is successively, 5.6 g of paraformaldehyde, 10 g of morpholine and 25 ml of concentrated HCl. The mixture is heated at reflux for 4 hours, cooled to room temperature (about 23° C.), diluted with acetone to 1 liter and the acetone dilution maintained at 0° C. overnight. The resultant precipitate of 1-(3,4-dichlorophenyl)-5-morpholin-4-yl-1-penten-3-one hydrochloride is filtered and recrystallized from ethanol/methanol (700/200 ml), collected by filtration and vacuum dried for 4 hours at 60° C. followed by 18 hours at room temperature; m.p. 199°–200° C.

C. Other Salts of 1-(3,4-dichlorophenyl)-5-morpholin-4-yl-1-penten-3-one: Analogously to Example 2, the hydrochloride salt prepared in Example 3B above, is converted to the free base. 550 mg of citric acid, 428 mg of tartaric acid and 274 mg of methanesulfonic acid are respectively added to individual portions of 2.85 mmols of the free base. Each solution is heated for 4 hours and is allowed to stand for 1–2 days.

The citrate was solidified with anhydrous ether and recrystallized from isopropyl alcohol, yielding (E)-1-(3,4-dichlorophenyl)-5-(4-morpholinyl)-1-penten-3-one citrate. The tartrate was recrystallized from ethyl alcohol, yielding 1.25 g of (E)-1-(3,4-dichlorophenyl)-5-(4-morpholinyl)-1-penten-3-one tartrate (m.p. 108°-110° C.). The methanesulfonic acid salt which had solidified was triturated with anhydrous ether and recrystallized from isopropyl alcohol, yielding (E)-1-(3,4-dichlorophenyl)-5-(4-morpholinyl)-1-penten-3-one methansulfonate hemihydrate (m.p. 105°-107° C.).

EXAMPLE 4

A. 4-(3-trifluoromethylphenyl)-3-buten-2-one: 10.0 g (46.3 mmoles) of m-trifluoromethyl cinnamic acid is dissolved in 300 ml of diethyl ether and the solution chilled to −70° C. 30 ml of a 1.8 molar solution of methyl lithium in ether is added dropwise with stirring. The stirring is maintained at −70° C. for 3 hours. The solution is raised to room temperature and stirred overnight. The mixture is then poured into an approximately equal volume of 1 N HCl and two layers obtained. The ether layer is separated and washed with aqueous HCl and then aqueous NaHCO$_3$. The ether extracts are dried (MgSO$_4$) and evaporated. The residue is distilled and the b.p. 90°-92° C./0.2 mm fraction of 4-(3-trifluoromethylphenyl)-3-buten-2-one is collected.

B. 5-(4-morpholinyl)-1-(3-trifluoromethylphenyl)-1-penten-3-one hydrochloride: A mixture of 5.0 g (23.3 mmoles) of 4-(3-trifluoromethylphenyl)-3-buten-2-one, 0.7 g (23.3 mmoles) of paraformaldehyde, 2.0 g (23.3 mmoles) of morpholine, 30 ml of ethanol and 5 ml of concentrated HCl is heated at reflux for 24 hours. The mixture is cooled and poured into 300 ml of acetone. The acetone solution is chilled overnight at about 0° C. The acetone is evaporated and the residue is recrystallized from ethanol, collected by filtration and vacuum dried overnight at 50° C. to produce 1.2 g of 5-(4-morpholinyl)-1-(3-trifluoromethylphenyl)-1-penten-3-one hydrochloride. m.p. 192°-193° C.

EXAMPLE 5

A. 4-(2,6-dichlorophenyl)-3-buten-2-one: 10 g of NaOH is dissolved in 250 ml of water and the solution is added to a solution of 20 g of 2,6-dichlorobenzaldehyde in 200 ml of acetone. The mixture is stirred for one hour at room temperature. Thin layer chromatography is used to determine complete reaction. The mixture is poured into 300 ml of water and the aqueous mixture is extracted with chloroform (2×300 ml). The chloroform layers are combined, dried and evaporated. The residue is distilled and the b.p. 102°-103° C./0.01 mm fraction is collected to yield 17.6 g of 4-(2,6-dichlorophenyl)-3-buten-2-one.

B. 1-(2,6-dichlorophenyl)-5-(4-morpholinyl)-1-penten-3-one hydrochloride: 5 g (0.023 mole) of the intermediate prepared in Example 5A is dissolved in 25 ml of ethanol. A mixture of 2 g (0.023 mole) of morpholine, 1.14 g (0.023 mole) of paraformaldehyde and 5 ml of concentrated hydrochloric acid is added thereto. The reaction mixture is refluxed overnight. The mixture is cooled to room temperature and diluted with acetone to a volume of 400 ml. The acetone dilution is maintained at 0° C. overnight. The resultant precipitate is collected by filtration and recrystallized from ethyl alcohol. The recrystallized precipitate of 1-(2,6-dichlorophenyl)-5-(4-morpholinyl)-1-penten-3-one hydrochloride is again collected by filtration and vacuum dried. m.p. 193°-194° C.

EXAMPLE 6

A. 4-(3,4-methylenedioxyphenyl)-3-buten-2-one: 10 g of NaOH is dissolved in 250 ml of water. The solution is added to a solution of 25 g of piperonal in 200 ml of acetone. The mixture is stirred at room temperature for one hour and is then poured into water. The resultant aqueous mixture is extracted with chloroform and the chloroform extract layers are dried and evaporated. The resultant precipitate is recrystallized from toluene to yield 20 g of 4-(3,4-methylenedioxyphenyl)-3-buten-2-one. m.p. 108°-109° C.

The same intermediate reaction product can also be prepared on a larger scale as follows. A 300 gallon glass-lined reactor is charged with 75 liters of deionized water. 27.0 kg (180 moles) of piperonal is dissolved in 51 liters (40.4 kg; 695 moles) of acetone and is added to the reactor. 2.7 kg (67.5 moles) of sodium hydroxide is dissolved in 12 liters of deionized water and is also charged into the reactor. An additional 675 liters of deionized water is added and the mixture stirred vigorously for about 8 hours. It is then stirred more slowly overnight at ambient temperature. The resultant solid is separated by filtration and washed with water. The washed crude material is dissolved in 250 liters of hot isopropyl alcohol and the solution is stirred and gradually cooled to 5° C. The recrystallized material is filtered off and washed with 10 liters of cold isopropyl alcohol. On the average, 32.0 kg of 4-(3,4-methylenedioxyphenyl)-3-buten-2-one is recovered. m.p. 106°-108° C. The filtrate is concentrated to recover the solvent and to obtain a second crop.

B. 1-(1,3-benzodioxol-5-yl)-5-(4-morpholinyl)1-penten-3-one hydrochloride: A mixture of 5 g (26.3 mmoles) of the intermediate product prepared in Example 6A, 12.3 g (26 mmoles) of morpholine, 1.4 g (26 mmoles) of paraformaldehyde, 25 ml of ethanol and 5 ml of concentrated hydrochloric acid is prepared by successive addition of the ingredients and the resultant solution is heated at reflux for 6 hours and overnight at room temperature. The reaction mixture is then poured into acetone and maintained at 0° C. overnight. The resultant crystals are filtered and recrystallized from ethanol. The recovered precipitate is separated by filtration and vacuum dried overnight to produce a product of 1-(1,3-benzodioxol-5-yl)-5-(4-morpholinyl)-1-penten-3-one hydrochloride. m.p. 188°-189° C.

EXAMPLE 7

A. 4-(4-methylthiophenyl)-3-buten-2-one: 15.2 g (0.1 mole) of 4-methylthiobenzaldehyde is dissolved in 25 ml of acetone. This solution is diluted with 40 ml of water and 6 ml of water containing 1.3 g of NaOH is added thereto. The mixture of diluted with 300 ml of water and stirred overnight. The resultant mixture is extracted with methylene chloride and the organic layer extracts are evaporated. The residue is recrystallized from toluene giving 8.1 g of 4-(4-methylthiophenyl)-3-buten-2-one. m.p. 99.5°-101° C.

B. (E)-1-[4-(methylthio)phenyl]-5-(4-morpholinyl)-1-pentene-3-one hydrochloride: A mixture of 3.8 g (0.02 mole) of the intermediate product prepared in Example 7A, 600 mg (0.02 mole) of paraformaldehyde, 1.74 g (0.02 mole) of morpholine, 40 ml of ethanol and 4 ml of concentrated HCl is heated at reflux for 18 hours. The resultant solution is diluted with acetone to a volume of 200 ml. The acetone dilution is chilled and maintained at 0° C. overnight. The resultant precipitate is separated by filtration and recyrstallized from ethanol. The filtered precipitate is vacuum dried at 50° C. to produce 1.7 g of (E)-1-[4-(methylthio)phenyl]-5-(4-morpholinyl)-1-penten-3-one hydrochloride. m.p. 195°–196° C.

EXAMPLE 8

A. 4-(4-methylsulfonylphenyl)-3-buten-2-one: 3.8 g (20 mmoles) of the product prepared in Example 7A (4-(4-methylthiophenyl)-3-buten-2-one) is dissolved in 100 ml of chloroform and the solution is chilled in an ice bath. There is added dropwise thereto 9.4 g of a 90% solution of m-chloroperbenzoic acid in chloroform (150 ml). After 4 hours at ice bath temperature, the solution is stirred overnight at room temperature. The mixture is extracted with 1 N NaOH. The organic layer is dried and evaporated. The residue is recrystallized from hexane yielding 2.6 g of 4-(4-methylsulfonylphenyl)-3-buten-2-one. m.p. 124°–125° C.

B. 5-(4-morpholinyl)-1-(4-methylsulfonylphenyl)-1-penten-3-one hydrochloride: 6.6 g (30 mmoles) of the intermediate product prepared in Example 8A, 1 g of paraformaldehyde and 27 g (30 mmoles) of morpholine are added to 60 ml of ethanol. There is then added thereto 6 ml of concentrated HCl and the solution is heated at reflux for 18 hours. The reaction solution is then diluted to 200 ml with acetone and maintained at 0° C. overnight. The resultant precipitate is separated by filtration and recrystallized from ethyl alcohol/methyl alcohol. The recrystallized product is vacuum dried at 55° C. to yield 2.4 g of the trans-isomer of 5-(4-morpholinyl)-1-(4-methylsulfonylphenyl)-1-penten-3-one hydrochloride. m.p. 191°–192° C.

EXAMPLE 9

A. 4-(4-chlorophenyl)-3-buten-2-one: To 75 ml of water was added a solution of 28 g of parachlorobenzaldehyde dissolved in 60 ml of acetone. A solution of 2.8 g of NaOH and 12 ml of water, and then a solution of 670 ml of water are added thereto. The reaction mixture is stirred overnight. The resultant precipitate was recrystallized from ethanol yielding 32 g of 4-(4-chlorophenyl)-3-buten-2-one. m.p. 47°–50° C.

B. 5-(4-morpholinyl)-1-(4-chlorophenyl)-1-penten-3-one hydrochloride: 6 g (30 mmoles) of the intermediate product prepared in Example 9A, 1 g (a 10% excess) of paraformaldehyde, 2.6 g (30 mmoles) of morpholine, 60 ml of ethanol and 6 ml of concentrated hydrochloric acid are mixed and the mixture is heated for 18 hours at reflux. The reaction mixture is then diluted to 200 ml wit acetone and is maintained at 0° C. overnight. The resultant precipitate is separated by filtration and is recrystallized from ethyl alcohol, yielding 3.1 g of 5-(4-morpholinyl)-1-(4-chlorophenyl)-1-penten-3-one hydrochloride. m.p. 204°–205° C.

EXAMPLE 10

A. 4-(4-cyanophenyl)-3-buten-2-one: To 30 ml of water is added a solution of 10 g of 4-cyanobenzaldehyde in 20 ml of acetone. A solution of 1 g of sodium hydroxide and 4 ml of water is added thereto, followed by 200 ml of water. The reaction mixture is stirred for 24 hours at room temperature. The resultant precipitate is filtered and recrystallized from the minimum amount of ethanol. 3 g of 4-(4-cyanophenyl)-3-buten-2-one is obtained. m.p. 103°–106° C.

B. 5-(4-morpholinyl)-1-(4-cyanophenyl)-1-penten-3-one hydrochloride: A mixture of 2.8 g of the intermediate product prepared in Example 10A (16.4 mmoles), 600 mg (1.5 equivalents) of paraformaldehyde, 1.4 g (16.4 mmoles) of morpholine, 40 ml of ethanol and 5 ml of concentrated HCl is heated at reflux for 18 hours. Thereafter, the reaction solution is diluted to 250 ml with acetone and is chilled to 0° C., at which temperature it remains overnight. The resultant precipitate is separated by filtration and is recrystallized from a mixture of ethyl alcohol and methyl alcohol. After vacuum drying, there is obtained 1.4 g of 5-(4-morpholinyl)-1-(4-cyanophenyl)-1-penten-3-one hydrochloride. m.p. 213°–214.5° C.

EXAMPLE 11

A. 4-(4-methoxyphenyl)-3-buten-2-one: A solution of 28 g of p-methoxybenzaldehyde, dissolved in 70 ml of acetone, is added to an equal volume of water and the reaction mixture is stirred vigorously. To the stirring mixture is added a solution of 2.8 g of sodium hydroxide dissolved in 15 ml of water, followed by an additional 600 ml of water. The resultant precipitate is collected by filtration, and dried and recrystallized from the minimum quantity of hexane to yield 4-(4-methoxyphenyl)-3-buten-2-one; m.p. 72°–73° C.

B. (E)-1-(4-methoxyphenyl)-5-(4-morpholinyl)-1-penten-3-one hydrochloride: 5.28 g (0.03 mole) of the product of Example 11A, 2.6 g (0.03 mole) of morpholine and 2 g (0.066 mole) of paraformaldehyde are added to 60 ml of ethanol. 6 ml of concentrated HCl is added to the solution and the mixture is heated at reflux temperature for 18 hours. The resultant mixture is diluted with acetone to 200 ml and chilled. The resultant solution is evaporated to a small volume and diluted with ethanol (100 ml). On standing at room temperature, crystals form. The precipitate is filtered and recrystallized from ethanol/methanol, yielding (E)-1-(4-methoxyphenyl)-5-(4-morpholinyl)-1-penten-3-one hydrochloride; m.p. 180°–181° C.

EXAMPLE 12

(E)-1-(4-methylphenyl)-5-(4-morpholinyl)-1-penten-3-one hydrochloride: 8 g (0.05 mole) of 4-(4-methylphenyl)-3-buten-2-one (prepared analogously to the intermediates for the foregoing examples), 2 g (a 30% excess) of paraformaldehyde and 4.35 g (0.05 mole) of morpholine are dissolved in a mixture of ethanol (60 ml) and concentrated HCl (6 ml). The mixture is heated at reflux temperature for 18 hours. The mixture is then cooled to room temperature and diluted with acetone to a volume of 250 ml. The solution is chilled overnight. It is then concentrated to a volume of about 25 ml. The residue is triturated with ethyl alcohol. The insoluble material is filtered and recrystallized from ethyl alcohol/methyl alcohol. The resultant crystals are filtered and vacuum dried overnight, yielding 3.3 g of (E)-1-(4-methylphenyl)-5-(4-morpholinyl)-1-penten-3-one hydrochloride; m.p. 188°–190° C.

EXAMPLE 13

(E)-1-(4-hydroxyphenyl)-5-(4-morpholinyl)-1-penten-3-one hydrochloride: 4.86 g (0.03 mole) of 4-(4-hydroxyphenyl)-3-buten-2-one, 1.2 g (0.04 mole) of paraformaldehyde and 2.6 g (0.03 mole) of morpholine is added to 60 ml of ethanol and 6 ml of concentrated HCl is added thereto. The mixture is heated at reflux temperature for 18 hours and then cooled to room temperature. The resultant mixture is diluted with acetone to a volume of 250 ml and subsequently chilled overnight. The insoluble material is filtered and recrystallized from a mixture of ethyl and methyl alcohols. The crystals are filtered and vacuum dried overnight, yielding (E)-1-(4-hydroxyphenyl)-5-(4-morpholinyl)-1-penten-3-one hydrochloride; m.p. 195°–196° C.

EXAMPLE 14

E-N,N,N-Trimethyl-3-oxo-5-phenyl-4-penten-1-aminium iodide:

Analogously to Examples 1 and 2, 4-phenyl-3-butene-2-one is reacted with paraformaldehyde, HCl and dimethylamine to produce 5-dimethylamino-1-phenyl-1-penten-3-one. 2.2 g of this amine and 16.1 g of methyl iodide are combined in 40 ml of diethyl ether and the mixture is stirred. After 10 minutes a white precipitate forms, and after 30 minutes, 50 ml of diethyl ether is added to maintain a stirrable slurry. The precipatate is filtered, washed with diethyl ether and dried in a dessicator to produce E-N,N,N-trimethyl-3-ox-5-phenyl-4-penten-1-aminium iodide, m.p. 204°–206° C.

EXAMPLE 15

The compounds of this invention can be administered topically to a patient as an antiviral agent, especially in the treatment of various manifestitations of herpes virus.

As the experimental results summarized above established, the compounds of this invention display antiviral effects in mice under conditions comparable to those under which administration of known antiviral agents such as phosphonoacetate achieves antiviral effects. Similar results can be established for other known antiviral agents such as vira-A (Parke Davis) or Stoxil (SKF). Thus, the compounds of this invention will be administered to humans, e.g., for the same indications as those seen in mice for such known compounds.

Of course, the dosage amounts for the compounds of this invention will be adjusted for their particular potencies as compared with those of such known agents as determined, for example, via the protocols discussed above or other conventional protocols.

For example, the compounds of this invention can be administered topically to a 70 kg adult 2–8 times per day in conventional topical formulations wherein it is present in a concentration of 1–10% based upon the total weight of the formulation, generally about 2–4%, e.g., for application to the epidermis for alleviation of symptoms of a herpes virus.

EXAMPLE 16

| Solution | |
|---|---|
| 1-(3,4-dichlorophenyl)-5-morpholin-4-yl-1-penten-3-one hydrochloride | 0.85 g |
| Alcohol | 78.9 ml |
| Isopropyl Myristate | 5.0 g |
| Polyethylene Glycol 400 (Av. M.W. 400) | 10.0 g |
| Purified Water sufficient to make | 100 ml |

Combine the alcohol, isopropyl myristate and polyethylene glycol 400 and disolve the drug substance therein. Add sufficient purified water to give 100 ml.

EXAMPLE 17

| Powder | |
|---|---|
| 1-(3,4-dichlorophenyl)-5-morpholin-4-yl-1-penten-3-one hydrochloride | 1% w/w |
| Silicon dioxide, anhydrous | 0.5% w/w |

| Powder -continued | |
|---|---|
| Corn starch, lactose, fine powder - each, with the total sufficient to make | 50 kg |

EXAMPLE 18

| Hand Lotion | |
|---|---|
| 5-(4-morpholinyl)-1-phenyl-1-penten-3-one hydrochloride | 0.15 g |
| Isostearic acid | 10.0 g |
| Stearic acid | 8.0 g |
| Poloxamer 235 | 5.0 g |
| Propylene glycol | 10.0 g |
| Deionized water sufficient to make | 100.0 ml |

EXAMPLE 19

| Liquid Soap | |
|---|---|
| 5-(4-morpholinyl)-1-phenyl-1-penten-3-one hydrochloride | 0.3 |
| Green soap tincture, NF | 100 ml |

EXAMPLE 20

| Liquid Detergent | |
|---|---|
| 1-(3,4-dichlorophenyl)-5-morpholin-4-yl-1-penten-3-one hydrochloride | 0.025 g |
| Miranol SM Concentrate ® (Miranol Chem. Co., Irvington, N.J.) (35% 1-Carboxymethyl-3,4-dihydro-1-(2-hydroxyethyl)-2-nonyl-1H—imidazolium hydroxide, disodium salt, 5% NaCl, pH 8.9–9.1) | 25.0 g |
| Laureth-4 (Monolauryl ethers of polyoxyethylene glycols containing an average of 4 oxyethylene groups) | 2.0 g |
| Deionized water sufficient to make | 100 ml |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of treating a viral infection amenable to topical treatment comprising topically administering to a patient afflicted with such a viral infection an antivirally effective amount of a compound of the formula

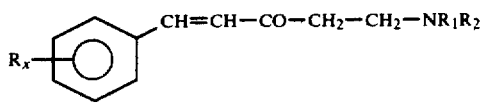

wherein

R is H, halo, $C_{1-4}$ alkyl, $C_{1-4}$ alkoxy, 3,4-methylenedioxy, $CF_3$, $NO_2$, $NH_2$, $N(C_{1-4}$ alkyl$)_2$, CN, OH, —S($C_{1-4}$ alkyl) or —SO$_2$($C_{1-4}$ alkyl); $R_1$ and $R_2$ are independently each H or $C_{1-4}$ alkyl or taken together with the attached N atom are morpholino, piperidino, pyrrolidino, piperazino, or N-$C_{1-4}$—alkyl piperazino; and, when R is halo, $C_{1-4}$ alkyl or $C_{1-4}$ alkoxy, x is 0-3 and, otherwise, is 0 or 1; or a pharmaceutically acceptable salt thereof with an acid or for the compounds wherein $R_1$ and $R_2$ are both not H, a quaternary ammonium salt thereof.

2. The method of claim 1 wherein the patient is afflicted with an infection mediated by a herpes virus.

3. The method of claim 1 wherein $R_x$ is H, monohalo or dihalo and $NR_1R_2$ is morpholino or dialkylamino.

4. The method of claim 3 wherein x is H, and $R_1$ and $R_2$ are methyl, said compounds being in the form of a quaternary ammonium salt.

5. The method of claim 1 wherein the compound administered is 5-(4-morpholinyl)-1-phenyl-1-penten-3-one or 5-(4-morpholinyl)-1-(3,4-dichlorophenyl)-1-penten-3-one or the hydrochloride salts thereof.

6. A quaternary salt of a compound of the formula

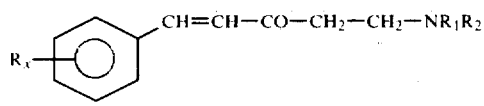

wherein R is H, halo, $C_{1-4}$ alkyl, $C_{1-4}$ alkoxy, 3,4-methylenedioxy, $CF_3$, $NO_2$, CN, OH, —S($C_{1-4}$ alkyl)or —$SO_2$($C_{1-4}$ alkyl); $R_1$ and $R_2$ are each $C_{1-4}$ alkyl or taken together with the attached N atom are morpholino, piperidino, pyrrolidino, piperazino, or N-$C_{1-4}$—alkyl piperazino; when R is halo, $C_{1-4}$ alkyl or $C_{1-4}$ alkoxy, x is 0-3 and, otherwise, is 0 or 1; or the free base and their acid addition salts of compounds of Formula I with the proviso that when R is H, $R_1$ and $R_2$ are not both alkyl or together with the attached N atom are not morpholino, pyrrolidino or piperidino; when $R_x$ is monochloro, $R_1$ and $R_2$ are not both dialkyl or together with the N atom to which they are attached are not morpholino or piperidino; when $R_x$ is dichloro, $R_1$ and $R_2$ are not both alkyl; when $R_x$ is monoalkyl, $R_1$ and $R_2$ are not both alkyl; when $R_x$ is dialkyl, $R_1$ and $R_2$ together with the N atom to which they are attached are not pyrrolidino; when R is mono- or di-alkoxy, $R_1$ and $R_2$ are not both alkyl and together with the N atom to which they are attached are not morpholino, pyrrolidino, or piperidino; when R is 3,4-methylenedioxy, $R_1$ and $R_2$ are not both alkyl and together with the N atom to which they are attached are not morpholino or piperidino; when R is $NO$, $R_1$ and $R_2$ are not both alkyl and together with the N atom to which they are attached are not morpholino, pyrrolidino or piperidino; when R is dialkylamino, $R_1$ and $R_2$ together with the N atom to which they are attached are not morpholino or piperidino; and when $R_x$ is OH and alkoxy, $R_1$ and $R_2$ are not both alkyl and together with the N atom to which they are attached are not morpholino, pyrrolidino or piperidino.

7. A compound of claim 6 wherein $R_3$ is H, monohalo or dihalo and $NR_1R_2$ is morpholino or dialkylamino.

8. A quaternary salt of a compound of claim 6 wherein the compound is 5-(4-morpholinyl)-1-(3,4-dichlorophenyl)-1-penten-3-one.

* * * * *